United States Patent
Carson

(10) Patent No.: US 9,642,711 B2
(45) Date of Patent: May 9, 2017

(54) HIGH FLEXION ARTICULAR INSERT

(75) Inventor: Christopher P. Carson, Collierville, TN (US)

(73) Assignee: Smith & Nephew, Inc., Memphis, TN (US)

( * ) Notice: Subject to any disclaimer, the term of this patent is extended or adjusted under 35 U.S.C. 154(b) by 1278 days.

(21) Appl. No.: 13/342,486

(22) Filed: Jan. 3, 2012

(65) Prior Publication Data

US 2012/0101586 A1    Apr. 26, 2012

Related U.S. Application Data

(63) Continuation of application No. 10/964,151, filed on Oct. 13, 2004, now abandoned.
(Continued)

(51) Int. Cl.
*A61F 2/38* (2006.01)
*A61F 2/30* (2006.01)
*A61F 2/46* (2006.01)

(52) U.S. Cl.
CPC ........ *A61F 2/3886* (2013.01); *A61F 2/30942* (2013.01); *A61F 2002/30133* (2013.01);
(Continued)

(58) Field of Classification Search
CPC ........ A61F 2/389; A61F 2/3868; A61F 2/461; A61F 2/385
See application file for complete search history.

(56) References Cited

U.S. PATENT DOCUMENTS 3,748,662 A    7/1973   Helfet
3,774,244 A    11/1973  Walker
(Continued)

FOREIGN PATENT DOCUMENTS

DE    3314038 A1    10/1983
DE    19529824 A1   2/1997
(Continued)

OTHER PUBLICATIONS

Communication Pursuant to Article 96(2) EPC in corresponding European Application No. 04794948.2, mailed Oct. 30, 2007, 5 pages.
(Continued)

*Primary Examiner* — Ann Schillinger
(74) *Attorney, Agent, or Firm* — Fish & Richardson P.C.

(57) ABSTRACT

A knee prosthesis is provided that allows for increased flexion. The knee prosthesis includes (a) a femoral component adapted to fit on a distal end of the femur which includes a lateral condylar structure and a medial condylar structure and (b) an intermediate structure configured to cooperate with a femoral component of a knee prosthesis. The intermediate structure includes at least one surface for contacting the femoral component and a transition of a sagittal curvature of the at least one contact surface from a concave surface into a convex surface at the contact interface of the femoral component and the intermediate structure when the knee is flexed at approximately 120° to 140°. The knee prosthesis minimizes impingement on the femoral posterior cortex in deep flexion, increases the dislocation safety factor and allows for easier reengagement of the articular surface should the femoral component externally rotate off of the tibial plateau.

53 Claims, 11 Drawing Sheets

Related U.S. Application Data

(60) Provisional application No. 60/512,457, filed on Oct. 17, 2003.

(52) U.S. Cl.
CPC ............. *A61F 2002/30388* (2013.01); *A61F 2002/30604* (2013.01); *A61F 2002/30616* (2013.01); *A61F 2002/30822* (2013.01); *A61F 2002/30878* (2013.01); *A61F 2002/30884* (2013.01); *A61F 2002/30957* (2013.01); *A61F 2002/4631* (2013.01); *A61F 2220/0025* (2013.01); *A61F 2230/0015* (2013.01); *A61F 2310/00029* (2013.01)

(56) References Cited

U.S. PATENT DOCUMENTS

| | | |
|---|---|---|
| 3,798,679 A | 3/1974 | Ewald |
| 3,816,855 A | 6/1974 | Saleh |
| 3,824,630 A | 7/1974 | Johnston |
| 3,924,277 A | 12/1975 | Freeman et al. |
| 3,958,278 A | 5/1976 | Lee et al. |
| 4,016,606 A | 4/1977 | Murray et al. |
| 4,178,641 A | 12/1979 | Grundei et al. |
| 4,207,627 A | 6/1980 | Cloutier |
| 4,209,861 A | 7/1980 | Walker et al. |
| 4,213,209 A | 7/1980 | Insall et al. |
| 4,249,270 A | 2/1981 | Bahler et al. |
| 4,309,778 A | 1/1982 | Buechel et al. |
| 4,340,978 A | 7/1982 | Buechel et al. |
| 4,353,135 A | 10/1982 | Forte et al. |
| 4,358,859 A | 11/1982 | Schurman et al. |
| 4,470,158 A | 9/1984 | Pappas et al. |
| 4,568,348 A | 2/1986 | Johnson et al. |
| 4,586,933 A | 5/1986 | Shoji et al. |
| 4,653,488 A | 3/1987 | Kenna et al. |
| 4,659,331 A | 4/1987 | Matthews et al. |
| 4,662,889 A | 5/1987 | Zichner et al. |
| 4,711,639 A | 12/1987 | Grundei |
| 4,714,472 A | 12/1987 | Averill et al. |
| 4,714,473 A | 12/1987 | Bloebaum |
| 4,721,104 A | 1/1988 | Kaufman et al. |
| 4,731,086 A | 3/1988 | Whiteside et al. |
| 4,770,663 A | 9/1988 | Hanslik et al. |
| 4,787,383 A | 11/1988 | Kenna |
| 4,822,365 A | 4/1989 | Walker et al. |
| 4,834,758 A | 5/1989 | Lane et al. |
| 4,865,606 A | 9/1989 | Rehder |
| 4,936,853 A | 6/1990 | Fabian et al. |
| 4,938,769 A | 7/1990 | Shaw |
| 4,944,756 A | 7/1990 | Kenna |
| 4,944,757 A | 7/1990 | Martinez et al. |
| 4,944,760 A * | 7/1990 | Kenna ............... 128/898 |
| 4,950,297 A | 8/1990 | Elloy et al. |
| 4,950,298 A | 8/1990 | Gustilo et al. |
| 4,959,071 A | 9/1990 | Brown et al. |
| 4,963,152 A | 10/1990 | Hofmann et al. |
| 5,007,933 A | 4/1991 | Sidebotham et al. |
| 5,021,061 A | 6/1991 | Wevers et al. |
| 5,032,134 A | 7/1991 | Lindwer |
| 5,035,700 A | 7/1991 | Kenna |
| 5,062,852 A | 11/1991 | Dorr et al. |
| 5,080,675 A | 1/1992 | Lawes et al. |
| 5,116,375 A | 5/1992 | Hofmann |
| 5,122,144 A | 6/1992 | Bert et al. |
| 5,133,758 A | 7/1992 | Hollister |
| 5,133,759 A | 7/1992 | Turner |
| 5,147,405 A | 9/1992 | Van Zile et al. |
| 5,147,406 A | 9/1992 | Houston et al. |
| 5,176,710 A | 1/1993 | Hahn et al. |
| 5,201,881 A | 4/1993 | Evans |
| 5,203,807 A | 4/1993 | Evans et al. |
| 5,219,362 A | 6/1993 | Tuke et al. |
| 5,226,916 A | 7/1993 | Goodfellow et al. |
| 5,236,461 A | 8/1993 | Forte |
| 5,263,498 A | 11/1993 | Caspari et al. |
| 5,282,867 A | 2/1994 | Mikhail |
| 5,282,870 A | 2/1994 | Moser et al. |
| 5,314,482 A | 5/1994 | Goodfellow et al. |
| 5,326,358 A | 7/1994 | Aubriot et al. |
| 5,326,361 A | 7/1994 | Hollister |
| 5,330,532 A | 7/1994 | Ranawat |
| 5,330,533 A | 7/1994 | Walker |
| 5,330,534 A | 7/1994 | Herrington et al. |
| 5,336,267 A | 8/1994 | Kubein-Meesenburg et al. |
| 5,358,527 A | 10/1994 | Forte |
| 5,358,529 A | 10/1994 | Davidson |
| 5,358,531 A | 10/1994 | Goodfellow et al. |
| 5,370,699 A | 12/1994 | Hood et al. |
| 5,370,701 A | 12/1994 | Finn |
| 5,395,401 A | 3/1995 | Bahler |
| 5,405,398 A | 4/1995 | Buford et al. |
| 5,413,604 A | 5/1995 | Hodge |
| 5,480,443 A | 1/1996 | Elias |
| 5,480,446 A | 1/1996 | Goodfellow et al. |
| 5,507,820 A | 4/1996 | Pappas |
| 5,514,143 A | 5/1996 | Bonutti et al. |
| 5,549,686 A | 8/1996 | Johnson et al. |
| 5,549,688 A | 8/1996 | Ries et al. |
| 5,549,689 A | 8/1996 | Epstein et al. |
| 5,556,432 A | 9/1996 | Kubein-Meesenburg et al. |
| 5,609,643 A * | 3/1997 | Colleran et al. ........... 623/20.29 |
| 5,609,645 A | 3/1997 | Vinciguerra |
| 5,611,802 A | 3/1997 | Samuelson et al. |
| 5,639,279 A | 6/1997 | Burkinshaw et al. |
| 5,658,342 A | 8/1997 | Draganich et al. |
| 5,658,344 A | 8/1997 | Hurlburt |
| 5,681,354 A | 10/1997 | Eckhoff |
| 5,683,468 A | 11/1997 | Pappas |
| 5,702,458 A | 12/1997 | Burstein et al. |
| 5,755,801 A | 5/1998 | Walker et al. |
| 5,755,803 A | 5/1998 | Haines et al. |
| 5,755,804 A | 5/1998 | Schmotzer et al. |
| 5,766,257 A | 6/1998 | Goodman et al. |
| 5,776,200 A | 7/1998 | Johnson et al. |
| 5,782,925 A | 7/1998 | Collazo et al. |
| 5,800,552 A | 9/1998 | Forte |
| 5,824,100 A | 10/1998 | Kester et al. |
| 5,824,102 A | 10/1998 | Buscayret |
| 5,871,545 A | 2/1999 | Goodfellow et al. |
| 5,871,546 A * | 2/1999 | Colleran ................. A61F 2/38 623/20.28 |
| 5,879,392 A | 3/1999 | McMinn |
| 5,906,643 A | 5/1999 | Walker |
| 5,935,173 A | 8/1999 | Roger et al. |
| 5,954,770 A | 9/1999 | Schmotzer et al. |
| 5,964,808 A | 10/1999 | Blaha et al. |
| 5,997,577 A | 12/1999 | Herrington et al. |
| 6,013,103 A | 1/2000 | Kaufman et al. |
| 6,039,764 A | 3/2000 | Pottenger et al. |
| 6,056,779 A | 5/2000 | Noyer et al. |
| 6,068,658 A | 5/2000 | Insall et al. |
| 6,074,425 A | 6/2000 | Pappas |
| 6,080,195 A | 6/2000 | Colleran et al. |
| 6,099,570 A | 8/2000 | Livet et al. |
| 6,120,543 A | 9/2000 | Kubein-Meesenburg et al. |
| 6,123,729 A | 9/2000 | Insall et al. |
| 6,139,581 A | 10/2000 | Engh et al. |
| 6,152,960 A | 11/2000 | Pappas |
| 6,165,223 A | 12/2000 | Metzger et al. |
| 6,190,415 B1 | 2/2001 | Cooke et al. |
| 6,203,576 B1 | 3/2001 | Afriat et al. |
| 6,206,926 B1 | 3/2001 | Pappas |
| 6,210,443 B1 | 4/2001 | Marceaux et al. |
| 6,235,060 B1 | 5/2001 | Kubein-Meesenburg et al. |
| 6,264,697 B1 | 7/2001 | Walker |
| 6,306,172 B1 | 10/2001 | O'Neil et al. |
| 6,325,828 B1 | 12/2001 | Dennis et al. |
| 6,361,564 B1 | 3/2002 | Marceaux et al. |
| 6,379,388 B1 | 4/2002 | Ensign et al. |
| 6,402,786 B1 | 6/2002 | Insall et al. |
| 6,406,497 B2 | 6/2002 | Takei |
| 6,413,279 B1 | 7/2002 | Metzger et al. |

(56) References Cited

U.S. PATENT DOCUMENTS

| | | |
|---|---|---|
| 6,428,577 B1 | 8/2002 | Evans et al. |
| 6,436,145 B1 | 8/2002 | Miller |
| 6,443,991 B1 | 9/2002 | Running |
| 6,475,241 B2 | 11/2002 | Pappas |
| 6,482,209 B1 | 11/2002 | Engh et al. |
| 6,485,519 B2 | 11/2002 | Meyers et al. |
| 6,491,726 B2 | 12/2002 | Pappas |
| 6,500,208 B1 | 12/2002 | Metzger et al. |
| 6,506,215 B1 | 1/2003 | Letot et al. |
| 6,558,426 B1 | 5/2003 | Masini |
| 6,569,202 B2 | 5/2003 | Whiteside |
| 6,575,980 B1 | 6/2003 | Robie et al. |
| 6,582,469 B1 | 6/2003 | Tornier |
| 6,589,283 B1 | 7/2003 | Metzger et al. |
| 6,620,198 B2 | 9/2003 | Burstein et al. |
| 6,623,526 B1 | 9/2003 | Lloyd |
| 6,652,587 B2 | 11/2003 | Felt et al. |
| 6,702,821 B2 | 3/2004 | Bonutti |
| 6,730,128 B2 | 5/2004 | Burstein |
| 6,755,864 B1 | 6/2004 | Brack et al. |
| 6,764,516 B2 | 7/2004 | Pappas |
| 6,770,097 B2 | 8/2004 | Leclercq |
| 6,770,099 B2 | 8/2004 | Andriacchi et al. |
| 6,811,568 B2 | 11/2004 | Minamikawa |
| 6,827,723 B2 | 12/2004 | Carson |
| 6,846,329 B2 | 1/2005 | McMinn |
| 6,866,683 B2 | 3/2005 | Gerbec et al. |
| 6,866,684 B2 | 3/2005 | Fell et al. |
| 6,887,276 B2 | 5/2005 | Gerbec et al. |
| 6,911,044 B2 | 6/2005 | Fell et al. |
| 6,972,039 B2 | 12/2005 | Metzger et al. |
| 6,984,249 B2 | 1/2006 | Keller |
| 7,048,741 B2 | 5/2006 | Swanson |
| 7,066,963 B2 | 6/2006 | Naegerl |
| 7,077,867 B1 | 7/2006 | Pope et al. |
| 7,081,137 B1 | 7/2006 | Servidio |
| 7,094,259 B2 | 8/2006 | Tarabichi |
| 7,104,996 B2 | 9/2006 | Bonutti |
| 7,160,330 B2 | 1/2007 | Axelson et al. |
| 7,261,740 B2 | 8/2007 | Tuttle et al. |
| 7,297,165 B1 | 11/2007 | Kriek |
| 7,326,252 B2 | 2/2008 | Otto et al. |
| 7,364,590 B2 | 4/2008 | Siebel |
| 7,371,240 B2 | 5/2008 | Pinczewski et al. |
| 7,422,605 B2 | 9/2008 | Burstein et al. |
| 7,686,812 B2 | 3/2010 | Axelson, Jr. et al. |
| 7,695,520 B2 | 4/2010 | Metzger et al. |
| 7,708,782 B2 | 5/2010 | Burstein et al. |
| 2001/0018615 A1 | 8/2001 | Biegun et al. |
| 2002/0055784 A1 | 5/2002 | Burstein et al. |
| 2002/0058997 A1 | 5/2002 | O Connor et al. |
| 2002/0103541 A1 | 8/2002 | Meyers et al. |
| 2002/0107576 A1 | 8/2002 | Meyers et al. |
| 2002/0120340 A1 | 8/2002 | Metzger et al. |
| 2002/0161447 A1 | 10/2002 | Salehi et al. |
| 2003/0009228 A1 | 1/2003 | Meyers et al. |
| 2003/0009230 A1 | 1/2003 | Gundlapalli et al. |
| 2003/0023314 A1 | 1/2003 | Burstein |
| 2003/0033018 A1 | 2/2003 | Merchant |
| 2003/0055501 A1 | 3/2003 | Fell et al. |
| 2003/0055509 A1 | 3/2003 | McCue et al. |
| 2003/0060882 A1 | 3/2003 | Fell et al. |
| 2003/0060883 A1 | 3/2003 | Fell et al. |
| 2003/0060884 A1 | 3/2003 | Fell et al. |
| 2003/0060885 A1 | 3/2003 | Fell et al. |
| 2003/0060888 A1 | 3/2003 | Fell et al. |
| 2003/0069591 A1 | 4/2003 | Carson et al. |
| 2003/0093156 A1 | 5/2003 | Metzger et al. |
| 2003/0100953 A1 | 5/2003 | Rosa et al. |
| 2003/0153977 A1 | 8/2003 | Suguro et al. |
| 2003/0153979 A1 | 8/2003 | Hughes et al. |
| 2003/0153980 A1 | 8/2003 | Brack |
| 2003/0163201 A1 | 8/2003 | McMinn |
| 2003/0199985 A1 | 10/2003 | Masini |
| 2003/0220697 A1 | 11/2003 | Justin et al. |
| 2004/0006393 A1 | 1/2004 | Burkinshaw |
| 2004/0030387 A1 | 2/2004 | Landry et al. |
| 2004/0034432 A1 | 2/2004 | Hughes et al. |
| 2004/0044414 A1 | 3/2004 | Nowakowski |
| 2004/0054416 A1 | 3/2004 | Wyss et al. |
| 2004/0064191 A1 | 4/2004 | Wasielewski |
| 2004/0102852 A1 | 5/2004 | Johnson et al. |
| 2004/0138755 A1 | 7/2004 | O'Connor et al. |
| 2004/0143339 A1 | 7/2004 | Axelson et al. |
| 2004/0162620 A1 | 8/2004 | Wyss |
| 2004/0199249 A1 | 10/2004 | Fell |
| 2004/0199250 A1 | 10/2004 | Fell |
| 2004/0204766 A1 | 10/2004 | Siebel |
| 2004/0243244 A1* | 12/2004 | Otto et al. ................. 623/20.27 |
| 2004/0249467 A1 | 12/2004 | Meyers et al. |
| 2004/0267363 A1 | 12/2004 | Fell et al. |
| 2005/0021147 A1 | 1/2005 | Tarabichi |
| 2005/0027365 A1 | 2/2005 | Burstein et al. |
| 2005/0033424 A1 | 2/2005 | Fell |
| 2005/0055102 A1 | 3/2005 | Tornier et al. |
| 2005/0096747 A1 | 5/2005 | Tuttle et al. |
| 2005/0107886 A1 | 5/2005 | Crabtree et al. |
| 2005/0143832 A1 | 6/2005 | Carson |
| 2005/0171604 A1 | 8/2005 | Michalow |
| 2005/0177169 A1 | 8/2005 | Fisher et al. |
| 2005/0209701 A1 | 9/2005 | Suguro et al. |
| 2005/0209703 A1 | 9/2005 | Fell |
| 2005/0246027 A1 | 11/2005 | Metzger et al. |
| 2006/0015109 A1 | 1/2006 | Haines |
| 2006/0015115 A1 | 1/2006 | Haines |
| 2006/0015116 A1 | 1/2006 | Haines |
| 2006/0015117 A1 | 1/2006 | Haines |
| 2006/0030853 A1 | 2/2006 | Haines |
| 2006/0030854 A1 | 2/2006 | Haines |
| 2006/0030855 A1 | 2/2006 | Haines |
| 2006/0030944 A1 | 2/2006 | Haines |
| 2006/0052875 A1 | 3/2006 | Bernero et al. |
| 2006/0058882 A1 | 3/2006 | Haines |
| 2006/0178749 A1 | 8/2006 | Pendleton et al. |
| 2006/0190087 A1 | 8/2006 | O'Connor et al. |
| 2006/0195195 A1 | 8/2006 | Burstein et al. |
| 2006/0212124 A1 | 9/2006 | Siebel |
| 2007/0078517 A1 | 4/2007 | Engh et al. |
| 2007/0282451 A1 | 12/2007 | Metzger et al. |
| 2008/0033567 A1 | 2/2008 | Stchur |
| 2008/0119940 A1 | 5/2008 | Otto et al. |
| 2008/0154270 A1 | 6/2008 | Haines et al. |
| 2009/0076514 A1 | 3/2009 | Haines |
| 2009/0164022 A1 | 6/2009 | Masini |
| 2009/0210066 A1 | 8/2009 | Jasty |
| 2009/0319047 A1 | 12/2009 | Walker |
| 2009/0319048 A1 | 12/2009 | Shah et al. |
| 2009/0319049 A1 | 12/2009 | Shah et al. |
| 2009/0326664 A1 | 12/2009 | Wagner et al. |
| 2009/0326667 A1 | 12/2009 | Williams et al. |
| 2010/0042224 A1 | 2/2010 | Otto et al. |
| 2010/0100192 A1 | 4/2010 | Haines et al. |
| 2010/0185203 A1 | 7/2010 | Haines |
| 2010/0305575 A1 | 12/2010 | Wilkinson et al. |
| 2011/0125280 A1 | 5/2011 | Otto et al. |
| 2011/0137619 A1 | 6/2011 | Otto et al. |

FOREIGN PATENT DOCUMENTS

| | | |
|---|---|---|
| EP | 189253 A2 | 7/1986 |
| EP | 336774 A1 | 10/1989 |
| EP | 381352 A1 | 8/1990 |
| EP | 420460 A1 | 4/1991 |
| EP | 510299 B1 | 8/1995 |
| EP | 529408 B1 | 12/1995 |
| EP | 923916 A1 | 6/1999 |
| EP | 988840 A1 | 3/2000 |
| EP | 941719 A3 | 9/2001 |
| EP | 1226799 A1 | 7/2002 |
| EP | 916321 B1 | 6/2003 |
| EP | 970667 B1 | 12/2003 |
| EP | 1285638 A3 | 12/2003 |
| EP | 1477143 A1 | 11/2004 |
| FR | 2702369 A1 | 9/1994 |

(56) References Cited

FOREIGN PATENT DOCUMENTS

| FR | 2710258 A1 | 3/1995 |
|---|---|---|
| FR | 2701387 B1 | 6/1995 |
| FR | 2760352 A1 | 9/1998 |
| GB | 1409150 A | 10/1975 |
| GB | 2007980 B | 7/1982 |
| GB | 2296443 A | 7/1996 |
| GB | 2312377 | 10/1997 |
| GB | 2324249 B | 12/2001 |
| GB | 2335145 B | 12/2002 |
| JP | 4951797 A | 5/1974 |
| JP | 5200057 A | 8/1993 |
| RU | 2121319 C1 | 11/1998 |
| WO | WO9322990 A1 | 11/1993 |
| WO | WO 9405212 | 3/1994 |
| WO | WO9603097 A1 | 2/1996 |
| WO | WO9623460 A1 | 8/1996 |
| WO | WO9624311 A1 | 8/1996 |
| WO | WO 9729703 | 8/1997 |
| WO | WO9927872 A1 | 6/1999 |
| WO | WO9930649 A1 | 6/1999 |
| WO | WO0113825 A1 | 3/2001 |
| WO | WO2004100839 A1 | 11/2004 |
| WO | WO 2009068951 | 6/2009 |
| WO | WO 2009105496 | 8/2009 |

OTHER PUBLICATIONS

Commuication Pursuant to Article 94(3) EPC in corresponding European Application No. 04794948.2, mailed Nov. 20, 2008, 3 pages.
Commuication Pursuant to Article 94(3) EPC in corresponding European Application No. 04794948.2, mailed Jul. 25, 2011, 5 pages.
Examiner's First Report on Australian Application No. 2004281743, mailed Aug. 27, 2009, 3 pages.
Examiner's Report No. 2 on Australian Application No. 2004281743, mailed May 20, 2011, 2 pages.
Office Action for Canadian Application No. 2,542,619, mailed Mar. 18, 2010, 2 pages.
Sathasivam, S., et al., "Optimization of the Bearing Surface Geometry of Total Knees," J. Biomechanics, vol. 27, No. 3, pp. 255-264, 1994.
Patent Examination Report No. 1 for Australian Application No. 2014200110, issued Oct. 22, 2014.
Patent Examination Report No. 2 for Australian Application No. 2011221425, mailed Jul. 12, 2012, 3 pages.
Brochure LCS® My knee. My life™ Family Brochure, DePuy, a Johnson & Johnson company, 21 pages 2008.
Brochure "Stryker Joint Replacement Scorpio NRG Non Restricted Geometry, Cruciate Retaining Knee System, Posterior Stabilized Knee System," 52 pages (Undated).
Brochure "TriathlonTM Knee System Design Rationale Surgical Instrumentation and Implants Knee Technology Designed for Natural Motion," 17 pages, 2004, Stryker.
Brochure entitled Online Orthopaedics, Total Knee Replacement, LCS® Complete Mobile-Bearing Knee System, p. 1-4 (May 1, 2010) http://www.orthopodsurgeon.com/kneereplace.html Accessed Jul. 23, 2010, (5 pages).
Buechel, FF, et al., "Low Contact Stress Meniscal Bearing Unicompartmental Knee Replacement: Long-Term Evaluation of Cemented and Cementless Results," Journal of Orthopaedic Rheumatology, presented at the 57th Annual American Academy of Orthopaedic Surgeons Meeting, New Orleans, LA, Feb. 11, 1990, Bates No. DEP00004096-DEP00004107, 13 pages.
Chiu, et al., "Bilateral Total Knee Arthroplasty: One Mobile-Bearing and One Fixed-Bearing," Journal of Orthopaedic Surgery, 2001, 9(1):45-50 (6 pages).
Desjardins, D., et al., "Interax Operative Techniques," Interax, 1994, Bates No. DEP00004391-DEP00004411, 22 pages.
Engh, G.A., et al., "The AMK Total Knee System, Design Rationale and Surgical Procedure," Published by DePuy, 1989, Bates No. DEP00004153-DEP00004201, 50 pages.
Exhibits 4, 5 and 8 from *Hudson Surgical Design, Inc. v. Zimmer Holdings, Inc., Zimmer Inc.*, Rush System for Health and Rush University Medical Center, Hudson Surgical Design, Inc.'s Opening Brief on Claim Construction Case No. 1:08-cv-01566, Civil Action No. 08C1566, Document No. 83, filed Nov. 17, 2008,7 pages.
Freeman, M.A.R., and Samuelson, K.M, Protek® Mark II Total Knee Replacement System, published 1985, 33 pages, attached as Exhibit G.
Haines et al., Accelerated Examination Search Statement and Support Document for Femoral Prosthetic Implant from U.S. Appl. No. 12/638,692, dated Dec. 15, 2009, 79 pages.
Haines et al., Corrected Accelerated Examination Search Statement and Support Document for Femoral Prosthetic Implant from U.S. Appl. No. 12/757,778, dated Apr. 9, 2010, 104 pages.
Protek F/S Modular Total Knee Replacement System, published by Protek, Jan. 1991, 59 pages, attached as Exhibit H.
Whiteside Ortholoc Total Knee System, Dow Corning Wright, pp. ZH0001 09679-ZH0001 09690, (13 pages).
Whiteside Ortholoc Total Knee System: Surgical Procedure, Dow Corning Wright, pp. WMT000001-WMT000040, Jun. 1985. (41 pages).
Zimmer, Insall/Burnstein II, Modular Knee System, Surgical Technique, pp. ZH000109691-ZH000109710, (21 pages).
Communication pursuant to Article 94(3) EPC for European Application No. 04794948.2, mailed Aug. 29, 2014.

* cited by examiner

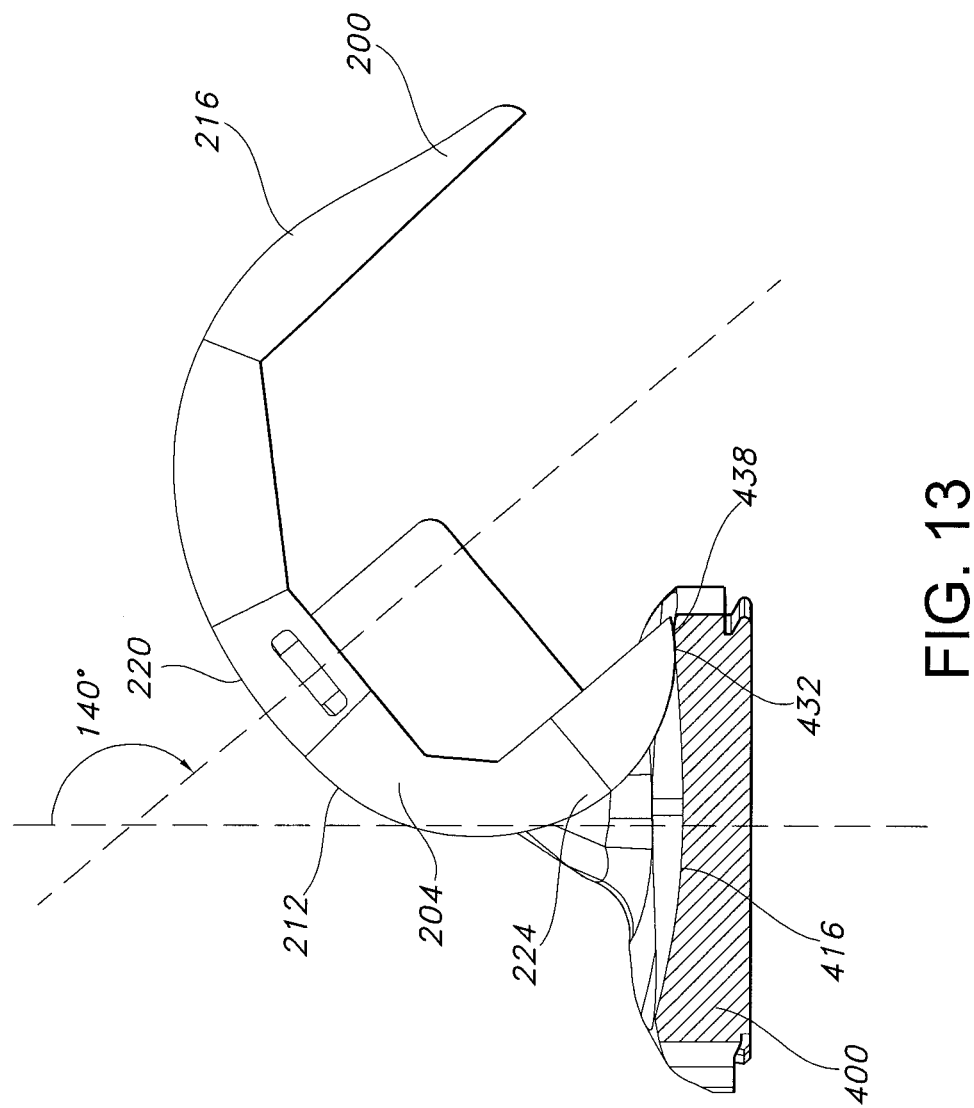

HIGH FLEXION ARTICULAR INSERT

CROSS REFERENCE TO RELATED APPLICATIONS

This application is a continuation of U.S. patent application Ser. No. 10/964,151, filed Oct. 12, 2004, which claims priority from U.S. Provisional Application Ser. No. 60/512,457, filed on Oct. 17, 2003. The prior applications are incorporated herein by reference in their entirety.

BACKGROUND OF THE INVENTION

1. Field of the Invention

The invention relates generally to knee prostheses and, more specifically, to knee prostheses which include the use of posterior stabilized inserts and have an extended range of flexion.

2. General Background of the Invention

Arthritis of the knee is a disease in which the surfaces of the knee gradually "wear out." Osteoarthritis, characterized by chronic degeneration of the cartilage of the joints, is the most common form of arthritis. This may be due to either old age, congenital deformity, or damage due to trauma. Osteoarthritis, characterized by chronic degeneration of the cartilage of the joints, is the most common form of arthritis. Systemic arthritis, such as rheumatoid arthritis, or gout affects the synovium (the membrane tissue in the joint that normally lubricates the joint), becomes pathologic and the surface of the joint is destroyed. In either case, when the surface of the joint is worn away, the activities of daily living can become very difficult. Standardized treatment such as weight loss, anti-inflammatory medication, braces, orthotics, steroid injections, physical therapy may be effective.

In many cases, however, despite the above non-surgical treatments, functional limitations persist. In such cases, disease and trauma affecting the articular surfaces of the knee joint are commonly treated by surgically replacing the ends of the femur and tibia with prosthetic femoral and tibial implants, referred to as total knee replacement (TKR).

In TKR surgery, a surgeon typically affixes two prosthetic components to the patient's bone structure; a first to the patient's femur and a second to the patient's tibia. These components are typically known as the femoral component and the tibial component respectively.

The femoral component is placed on a patient's distal femur after appropriate resection of the femur. The femoral component is usually metallic, having a highly polished outer condylar articulating surface, which is commonly J-shaped.

A common type of tibial component uses a tray or plateau that generally conforms to the patient's resected proximal tibia. The tibial component also usually includes a stem that extends at an angle to the plateau in order to extend into a surgically formed opening in the patient's intramedullary canal. The tibial component and tibial stem are both usually metallic.

A plastic or polymeric (often ultra high molecular weight polyethylene) insert or bearing fits between the tray of the tibial component and the femoral component. This tibial insert provides a surface against which the femoral component condylar portion articulates, i.e., moves in gross motion corresponding generally to the motion of the femur relative to the tibia.

In some knee prostheses, the insert also engages in motion relative to the tibial tray. Such motion can be translational and/or rotational sliding motion relative to the tibial plateau.

In other types of knee prostheses with tibial inserts, the tibial inserts can engage in other types of motion relative to the tibial plateau and/or femoral component.

Modern TKR's are tricompartmental designs; they replace three separate articulating surfaces within the knee joint: the patello-femoral compartment and the lateral and medial inferior tibio-femoral compartments. Most TKR's are designed to articulate from a position of slight hyperextension to approximately 115 to 130° flexion. A tricompartmental design can meet the needs of most TKR patients even though the healthy human knee is capable of a range of motion (ROM) approaching 170°. However, there are some TKR patients who have a particular need to obtain high flexion in the knee joint. For many, a TKR that permits patients to achieve a ROM in excess of 130° is desirable to allow deep kneeling, squatting and sitting on the floor with the legs tucked underneath.

Another problem encountered by TKR patients is unwanted movement of the femoral component on the tibial component. This occurs when the ligaments of the knee are "tight," or not tensioned properly, during the TKR procedure. Ligaments located on the side of the knee where the deformity is present become tight due to contraction of the compartment. A tight posterior cruciate ligament may cause the knee to move in an unnatural motion. A posterior stabilized insert may assist in preventing the femoral component from unnatural motion on the tibial component by providing posterior support after the posterior cruciate ligament is removed. However, current inserts providing posterior support are designed to allow a ROM to only about 120°. When a patient with a standard posterior support insert demands deeper flexion, the proximal edge of the femoral condyle edge loads into the posterior edge of the insert. This can lead to excessive polyethylene wear. The extreme posterior location of the contact point may also lead to lateral condylar subluxation as the tibia internally rotates. Deeper flexion also leads to increased femoral translation to the posterior edge of the insert. In conforming knee designs, this can limit range of motion because more implant material is located on the posterior edge of the insert. As the femoral component engages the thicker part of the insert, the lateral and medial collateral ligaments reach their strain limit, thus preventing further posterior translation and limiting flexion by impinging the posterior edge of the insert against the posterior cortex of the femur. Thus, there is a need for an insert that provides sufficient posterior support and reduces posterior conformity. Also needed is an insert that allows a ROM beyond 120° and minimizes polyethylene wear and accommodates condylar rotation.

BRIEF SUMMARY OF THE INVENTION

The invention provides various embodiments of improved knee prostheses for replacing at least a portion of a knee joint between the distal end of a femur and the proximal end of a tibia.

According to certain aspects and embodiments of the invention, there is provided a knee prosthesis including a femoral component adapted to fit on a distal end of a femur, the femoral component including a lateral condylar structure and a medial condylar structure and an intermediate structure configured to cooperate with the femoral component. The intermediate structure includes a proximal surface adapted to cooperate with an outer surface of the femoral component to allow flexion of the knee greater than 130°.

According to certain aspects and embodiments of the invention, there is further provided a knee prosthesis including a femoral component adapted to fit on a distal end of a femur, the femoral component including a lateral condylar structure and a medial condylar structure and an intermediate structure configured to cooperate with the femoral component, wherein the intermediate structure includes a proximal surface with an articular blend at the contact interface of the femoral component and the intermediate structure when the knee is flexed approximately 120° to 140°.

According to certain aspects and embodiments of the invention, there is further provided a knee prosthesis including a femoral component adapted to fit on a distal end of a femur, the femoral component including a lateral condylar structure and a medial condylar structure and an intermediate structure configured to cooperate with the femoral component. Here, the intermediate structure includes at least one surface for contacting the femoral component on a proximal surface of the intermediate structure between the intermediate structure and the femoral component the contact surface includes a curvature in the sagittal plane which transitions, in a posterior direction, from a concave surface into a convex surface at a contact point between the femoral component and the intermediate structure when the knee prosthesis is flexed at approximately 120° to 140°.

According to certain aspects and embodiments of the invention, there is provided a knee prosthesis having a femoral component adapted to fit on a distal end of a femur, the femoral component including a lateral condylar structure and a medial condylar structure and an intermediate structure configured to cooperate with the femoral component. The intermediate structure includes at least one surface for contacting the femoral component, a transition of a sagittal curvature of the contact surface from a concave surface into a convex surface, the transition occurring at a contact point between the femoral component and the intermediate structure when the knee prosthesis is flexed at approximately 120° to 140°, and a post adapted to provide posterior support to the femoral component, the post being adapted to minimize impingement on a patellar component when the knee is flexed approximately 130° or greater.

BRIEF DESCRIPTION OF THE SEVERAL VIEWS OF THE DRAWINGS

FIG. 13 is a side cross-sectional view of the knee prosthesis of FIG. 10 showing flexion of the knee at 140°.

DETAILED DESCRIPTION OF THE INVENTION

Various embodiments of the invention provide improved knee prostheses for replacing at least a portion of a knee joint between the distal end of a femur and the proximal end of a tibia.

As used herein, the following directional definitions apply. Anterior and posterior mean toward the front or toward the back of the body, respectively. Proximal means nearer to a point of reference, as opposed to distal which means farther from a point of reference. For example, the distal femur is part of the knee joint, while the proximal femur is part of the hip joint. Medial means nearer to the middle or center of the body. Lateral means farther from the middle or center of the body. Thus, when referring to the knee, medial would mean the side of the knee that is closest to the other knee and lateral would mean the side of the knee that is farthest from the other knee.

Knee prostheses according to certain embodiments of the invention advantageously remove material from the posterior edge of the insert that may impinge on the femoral posterior cortex (or corresponding portions of a femoral component) in deep flexion. Additionally, the 160° flexion contact point is moved anteriorly on the insert and distally on the femoral component to reduce edge loading. The anterior shift in flexion contact also increases the dislocation safety factor in deep flexion. Finally, should the lateral posterior condyle of the femoral component externally rotate off of the tibial plateau, as may occur in the normal knee in deep flexion, it will more easily engage the articular surface as the knee returns to extension.

The invention also maintains conventional amounts of femoral resection and utilizes existing instrumentation so that a surgeon may decide intraoperatively whether to use a standard posterior stabilized insert or the high flexion posterior stabilized insert of the invention.

Figure 1A:
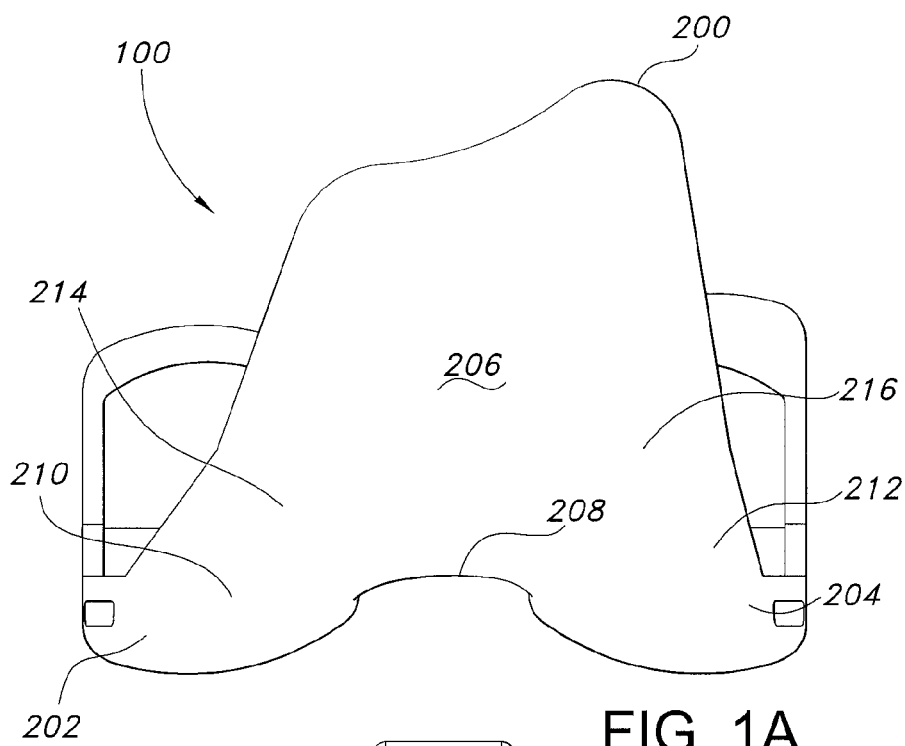
FIGS. 1A-1C show an exploded front view of a knee prosthesis according to an embodiment of the invention.
Figure 1B:
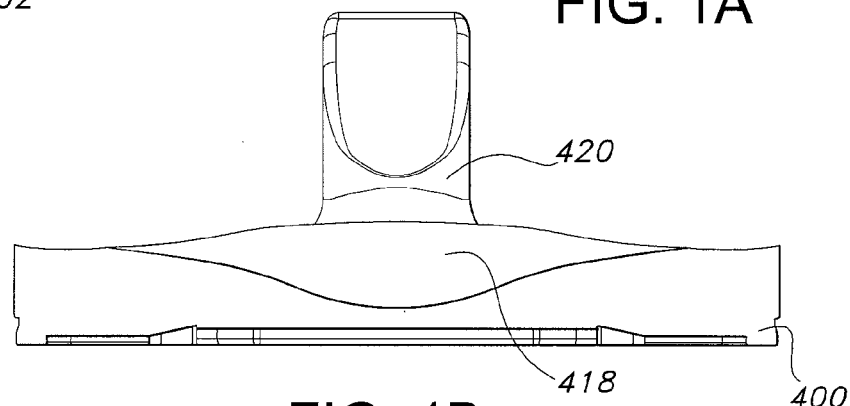
Figure 1C:
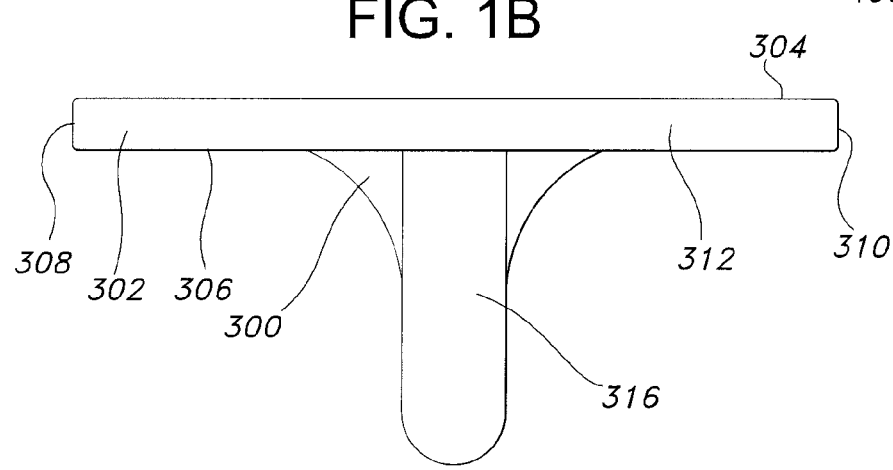

A preferred embodiment of a knee prosthesis according to the invention is shown in FIGS. 1A-1C and identified by the numeral 100. The knee prosthesis 100 is designed to replace at least a portion of a left knee joint between the distal end of a femur and the proximal end of a tibia. A mirror image of knee prosthesis 100 (not shown) will replace at least a portion of a right knee between the distal end of a femur and the proximal end of a tibia.

The knee prosthesis 100 includes a femoral component 200 for mounting to a distal end of a femur, a tibial component 300 for mounting to a proximal end of a tibia, and an intermediate component, such as articular insert 400.

Although a knee prosthesis 100 including an asymmetrical femoral component 200 is shown, symmetrical femoral components are also included within the scope of the invention. The femoral component 200 preferably includes a medial condylar portion 202, a lateral condylar portion 204 and a patellar flange portion 206 joining the anterior portions 214, 216 ends of the medial and lateral condylar portions 202, 204 together. The medial and lateral condylar portions 202, 204 are substantially parallel to each other and are spaced apart from one another to form an intercondylar recess or notch 208. Each condylar portion 202, 204 has an outer surface 210, 212 for engaging a portion of the tibial component 300 in an articulating fashion as will become apparent. The outer surfaces 210, 212 of each condylar portion 202, 204 preferably have a distal portion 218, 220 for engaging a portion of the tibial component 300 when the knee joint is extended and partially flexed, and a posterior portion 222, 224 (shown in FIG. 2) for engaging a portion of the tibial component 300 when the knee joint 102 is flexed substantially 90°.

The femoral component 200 may include typical attachment aids for helping to secure the femoral component 200 to a distal end of a femur. Such attachment aids may include one or more pegs, fins, surface treatments, cement or other conventional or nonconventional structure or technologies.

The tibial component 300 includes a tray or base member 302 for being secured to a proximal end of a tibia, and a stabilizing post 316, which is insertable into the tibial medullary canal and provides for the stabilization of the tibial component 300 on the tibia.

Figure 2:
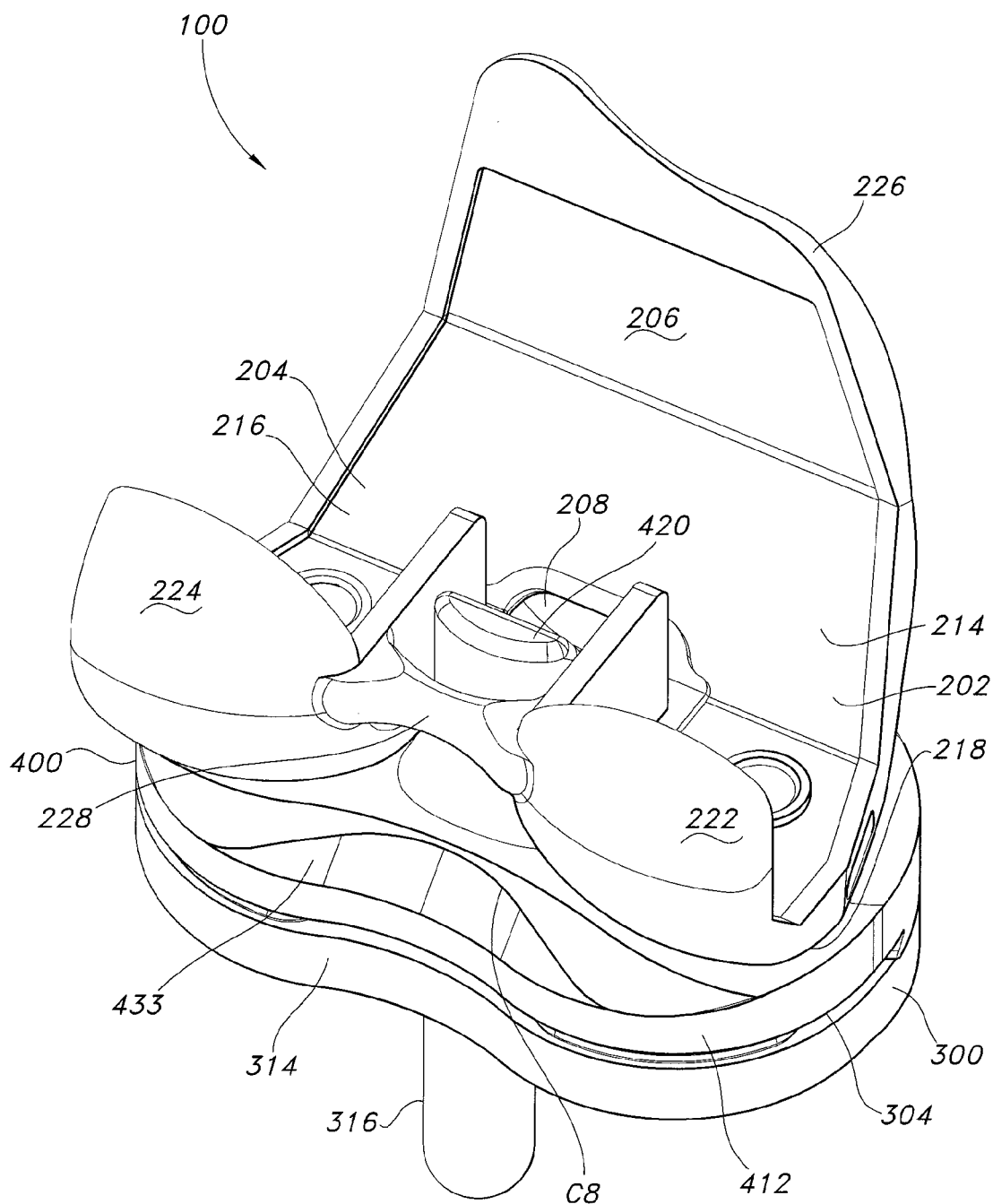
FIG. 2 is a back perspective view of a knee prosthesis according to an embodiment of the invention.

The tray member 302 has a proximal or upper surface 304, a distal or lower surface 306, a medial side 308, a lateral side 310, an anterior or front side 312, and a posterior or rear side 314 (shown in FIG. 2). The proximal surface 304 may be substantially flat and planar. The tray member 302 preferably includes attachment aids for helping to secure the tray member 302 to a proximal end of a tibia. Such attachment aids may include one or more pegs, fins, screws, surface treatments, etc.

The femoral component 200 and tibial component 300 may be constructed in various manners and out of various materials. For example, the femoral component 200 and tibial component 300 may be machined, cast, forged or otherwise constructed as a one-piece integral unit out of a medical grade, physiologically acceptable metal such as a cobalt chromium alloy or the like, in various sizes to fit a range of typical patients, or may be custom-designed for a specific patient based on data provided by a surgeon after physical and radiography examination of the specific patient.

Figure 4:
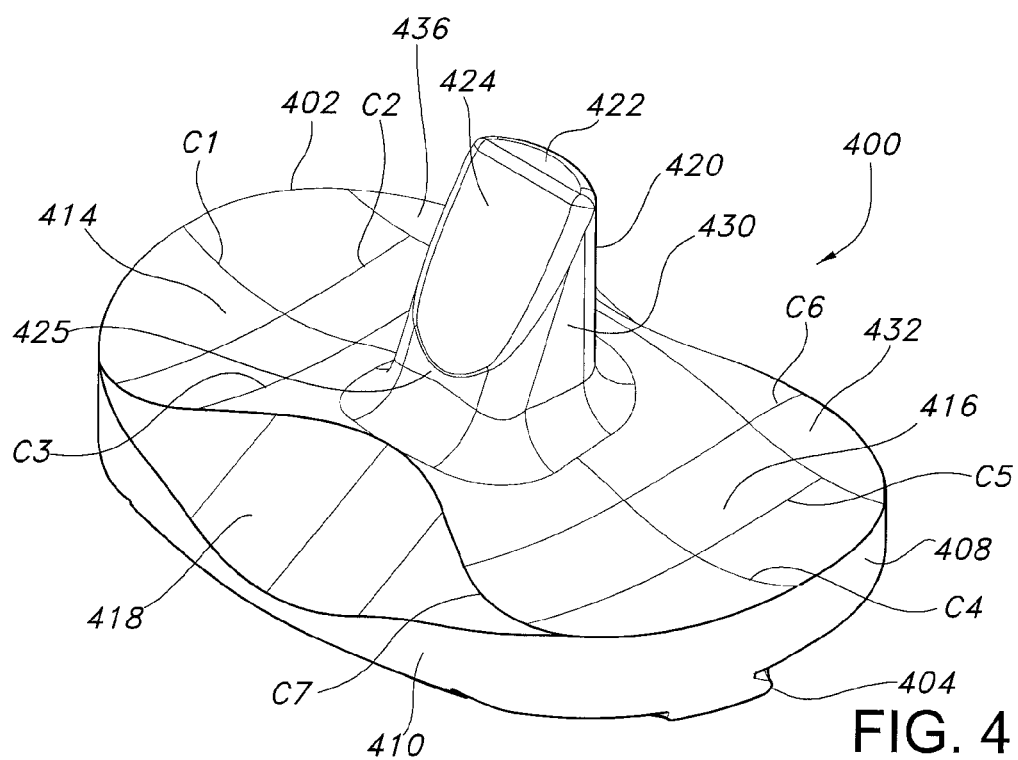
FIG. 4 is a perspective view of an articular insert according to an embodiment of the invention.

As shown in FIG. 4, the articular insert 400 has a proximal or upper surface 402, a distal or lower surface 404, a medial side 406 (shown in FIG. 5), a lateral side 408, an anterior or front side 410, and a posterior or rear side 412 (shown in FIG. 2). Although the medial and lateral sides 406, 408 (shown in FIG. 5) are separately identified, the insert 400 may be substantially symmetrical so that the medial and lateral sides 406, 408 are substantially the same or are identical.

The proximal surface 402 of the insert 400 has a medial concave portion 414 for engaging the outer surface 210 of the medial condylar portion 202 of the femoral component 200 in an articulating relationship, and a lateral concave portion 416 for engaging the outer surface 212 of the lateral condylar portion 204 of the femoral component 200 in an articulating relationship. Medial concavity 414 is defined by curves C1, C2, and C3. In the front or coronal plane, curve C1 has a radius of curvature of approximately 1.05 inches. In the sagittal plane, curves C2 and C3 have varying radii of curvature of approximately 2.88 to 3.05 inches. The radii of curvature can vary as desired. The radii may also vary according to component size. In a preferred embodiment, lateral concavity 416 is similar to medial concavity 414 and includes corresponding curves C4, C5 and C6.

Figure 3:
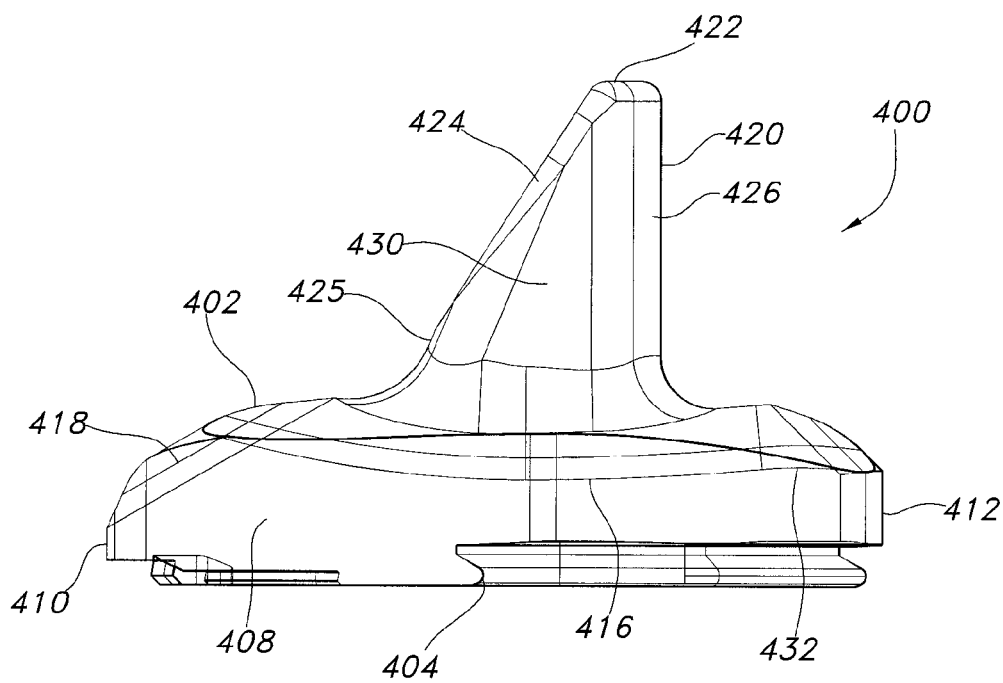
FIG. 3 is a side elevation view of an articular insert according to an embodiment of the invention.
Figure 5:
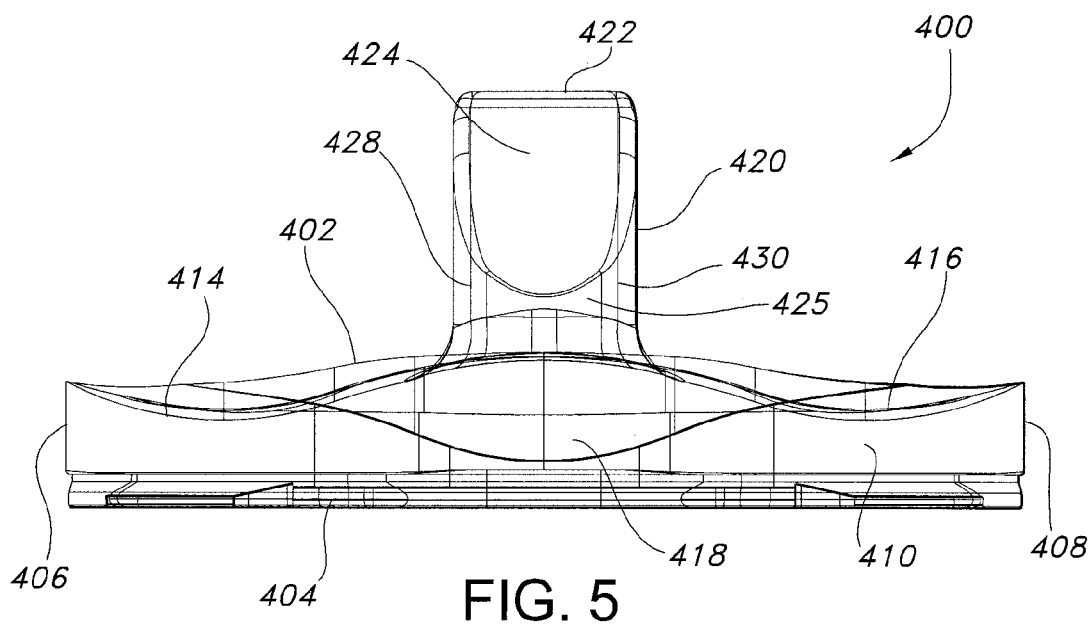
FIG. 5 is a front elevation view of an articular insert according to an embodiment of the invention.

As shown in FIGS. 3-5, the insert includes a central post 420. The post 420 has a proximal surface 422, anterior surface 424, posterior surface 426 and side surfaces 428, 430. In a preferred embodiment of the invention, the proximal surface 422 of the central post 420 preferably is parallel with distal surface 404. The anterior surface 424 of central post 420 in this embodiment is tapered at an angle of approximately 33° with respect to the distal surface 404 of the insert 400 to minimize impingement of the patella or a patellar implant (not shown) in deep flexion. The base 425 is tapered 23° in a posterior direction from anterior surface 424 to minimize impingement of the intercondylar notch 208 of femoral component 200 in hyperextension.

The insert 400 may include a curved anterior surface 418, as shown in FIG. 4. The curved anterior surface 418 has a curve C7 with central radius of curvature varying between approximately 1.5 to 2.5 inches, lateral to medial, as a general matter. Again, radii of curvature can vary as desired. The sagittal center line of the anterior curved surface 418 is oriented at approximately 30° to 45° above the distal surface 404 of the insert 400. When the insert 400 is attached to the tibial component 300, the curved anterior surface 418 begins approximately 2 mm above the tray member 302 of the tibial component 300 to allow room for the patellar tendon (not shown).

The insert 400 preferably includes articular blends 432, 436 on the lateral and medial sides of the insert 400. Articular blends 432, 436 are similar and articular blend 432 is described in detail below. The articular blend 432 begins at the contact interface of the femoral component 200 and the insert 400 (the femorotibial contact point 438) when the knee is flexed at approximately 120° to 140°. One result of using an articular blend 432 is that the posterior side 412 of the insert 400 is lowered and flexion joint space is maintained. In the sagittal plane, the articular blends 432, 436 (shown in FIG. 4) have a single sagittal radius of approximately 1.0 inch. Thus, as shown in FIG. 3, the articular blend 432 has a single sagittal radius of approximately 1.0 inch. However, the radius may vary and may feature any radius or radii as circumstances dictate or suggest.

Figure 10:
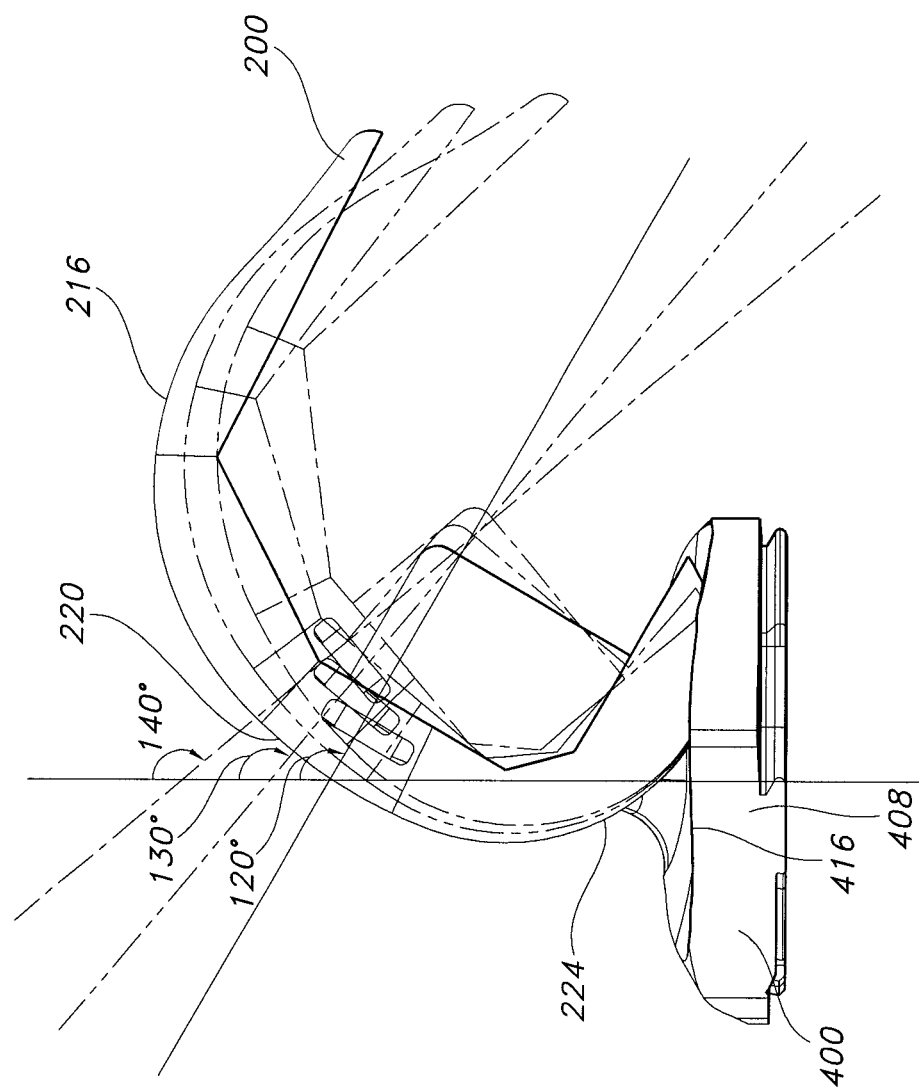
FIG. 10 is a side cross-sectional view of a partially assembled knee prosthesis including a size 5 femoral component on a size 5-6 insert according to an embodiment of the invention showing the range of flexion from 120° to 140°.
Figure 11:
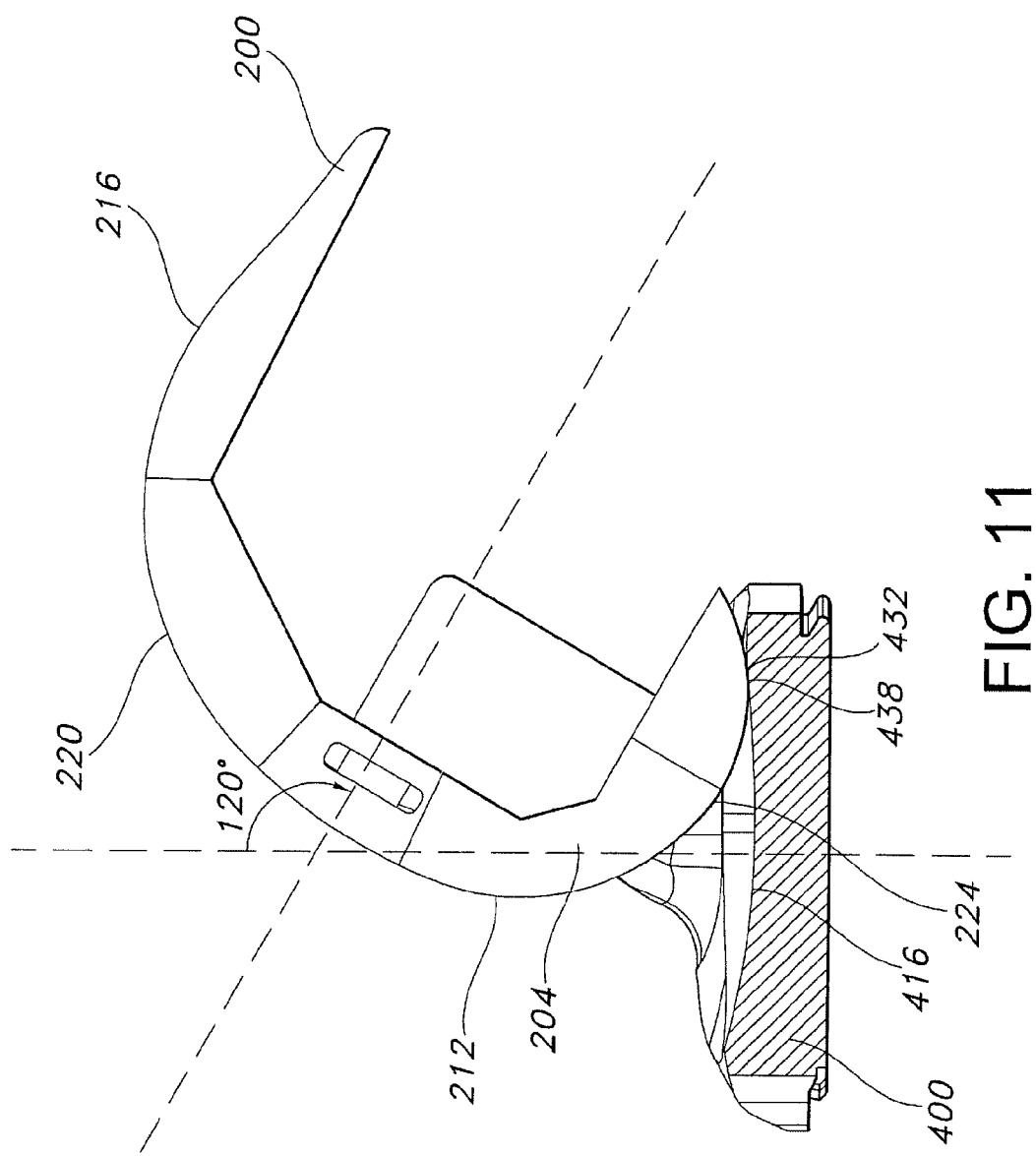
FIG. 11 is a side cross-sectional view of the knee prosthesis of FIG. 10 showing flexion of the knee at 120°.
Figure 12:
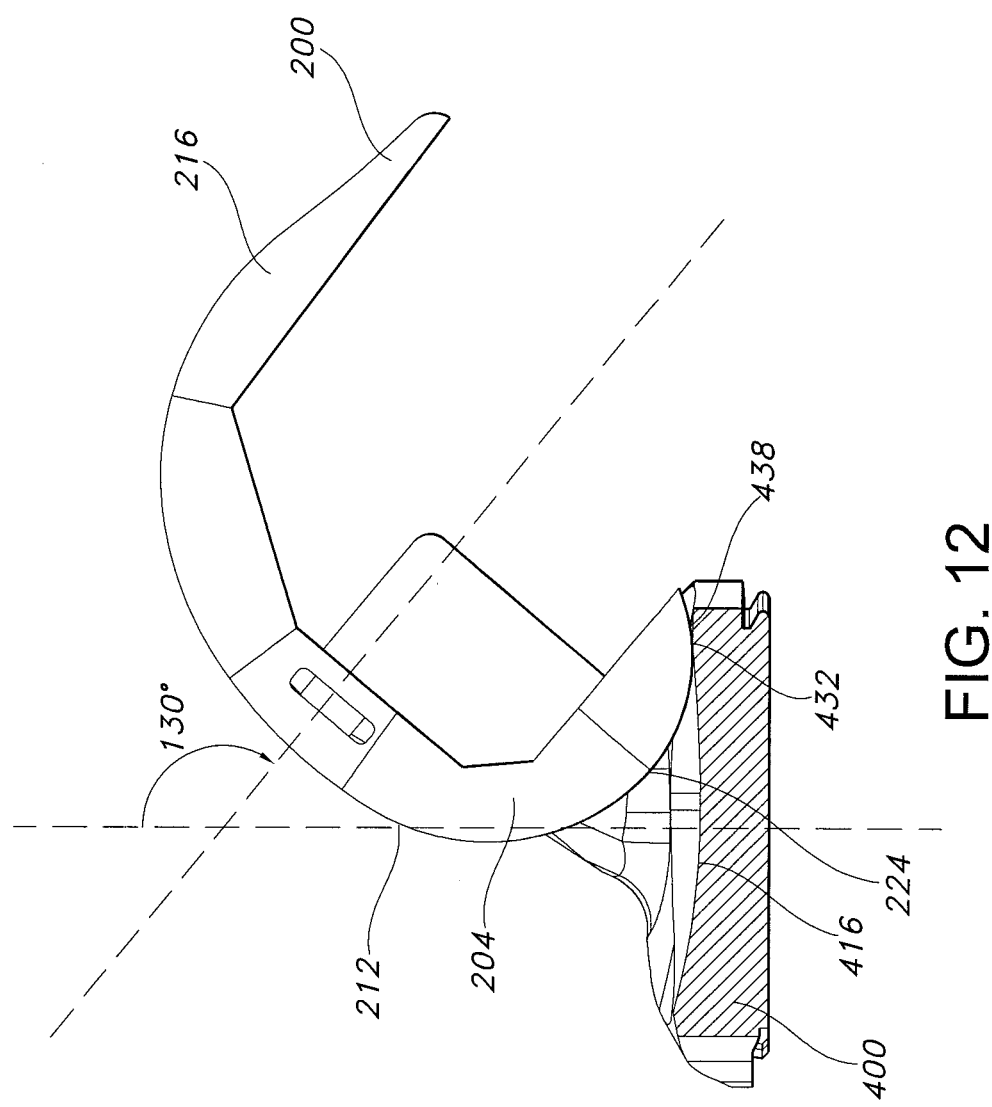
FIG. 12 is a side cross-sectional view of the knee prosthesis of FIG. 10 showing flexion of the knee at 130°.

The articular blends 432, 436 increase the amount of flexion allowed by the knee prosthesis 100 through the use of a transition or blend of the sagittal concave curvatures of the lateral and medial concavities, 414, 416 into a convex surface. The precise location of the articular blends 432, 436 varies depending on the size of the femoral component 200 and the size of the articular insert 400. However, the articular blend will generally begin at a point defined as the point of contact between the femoral component and the insert (the femorotibial contact point 438) when the femoral component is at a flexion angle of approximately 120° to 140°. For example, FIG. 10 illustrates the range of flexion from 120° to 140° of a size 5 femoral component on a size 5-6 insert. At 120° (also shown in FIG. 11), the posterior portion 224 of outer surface 212 of lateral condylar portion 204, has not yet engaged the articular blend 432. However, at 130° (also shown in FIG. 12), the posterior portion 224 of outer surface 212 of lateral condylar portion 204 directly engages the articular blend 432 at the femorotibial contact point, as shown in FIG. 12. At 140° (also shown in FIG. 13), the posterior portion 224 of outer surface 212 of lateral condylar portion 204 is past the beginning of the articular blend 432 at the femorotibial contact point 438 is on the convex surface of articular blend 432. Thus, as a general matter, as the femorotibial contact point 438 moves in a posterior direction, the proximal surface 402 of the insert 400 transitions from concave to convex.

As shown in FIG. 2, the insert may include a curved posterior surface 433, which is multi-radius. The curved posterior surface 433 has a curved surface C8 with a varying radius of curvature, lateral to medial. The result of the curved posterior surface 433 is the removal of material that may impinge on the posterior cortex of the femur in deep flexion. The radius of curvature may vary as desired to provide sufficient room for maximal flexion.

Figure 6:
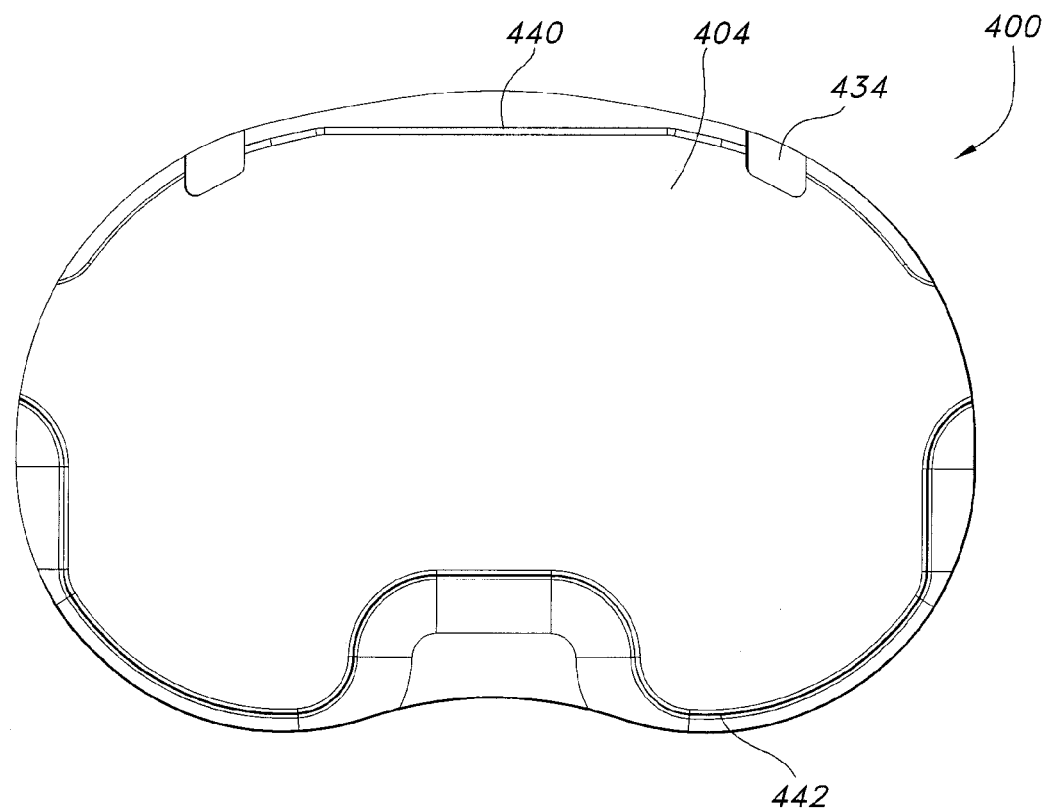
FIG. 6 is a bottom plan view of an articular insert according to an embodiment of the invention.

As shown in FIG. 6, the distal surface 404 of the insert 400 may be substantially flat or planar for contacting the proximal surface 304 of the tray member 302 of the tibial component 300. The distal surface 404 preferably includes a dovetail locking mechanism 434 that consists of an anterior portion 440 and a posterior portion 442, however, any conventional method for disposing the insert relative to the tray member 302, whether constrained or unconstrained, may be used.

In a preferred embodiment, a size 5-6 insert 400 has the following dimensions. The overall width of the insert 400 is approximately 2.913 inches from medial side 406 to lateral side 408. The depth of the insert 400 is approximately 1.944 inches from anterior side 410 to posterior side 412. The thickness of the insert 400 at the medial and lateral sides 406, 408 varies, ranging from approximately 0.381 to 1.011 inches. The thickness of the insert 400 at the posterior side 412 ranges from approximately 0.548 to 1.178 inches. The width of the anterior curved surface 418 ranges from approximately 1.869 to 2.421 inches. At the outermost edges of the anterior curved surface 418, the thickness of the insert 400 ranges from approximately 0.408 to 1.001 inches. The central post 420 is approximately 0.560 inches wide. Its height, from the distal surface 404 of the insert 400, ranges from approximately 1.259 to 1.889 inches. These dimensions have a tolerance ranging from approximately +/−0.005 to 0.020 inches.

The insert 400 may be constructed in various manners and from various materials. For example, the insert 400 may be machined, molded or otherwise constructed as a one-piece, integral unit out of medical grade, physiologically acceptable plastic such as ultra high molecular weight polyethylene or the like, in various sizes to fit a range of typical patients, or may be custom-designed for a specific patient based on data provided by a surgeon after physical and radiographic examination of the specific patient. The material can be treated, for example, by radiation, chemistry, or other technology to alter its wear properties and/or strength or hardness. An articular insert 400 constructed of ultra high molecular weight polyethylene will freely slide on a polished upper surface of the tray member 302 of the tibial component 300, thereby reducing material wear.

As shown in FIG. 2, when the knee prosthesis 100 is assembled, the central post 420 of the insert 400 fits within the intercondylar recess 208. The posterior stabilized femoral component 226 includes a horizontal connection member, or cam, 228 between the posterior portions 222, 224 of the condylar portions 202, 204. The distal portions 218, 220 of the condylar portions 222, 224 rest on the medial and lateral concavities 414, 416 of the insert 400. Because the femoral component 226 and the insert 400 are not fastened to each other, the femoral component 226 is able to easily move on the insert 400.

Figure 7:
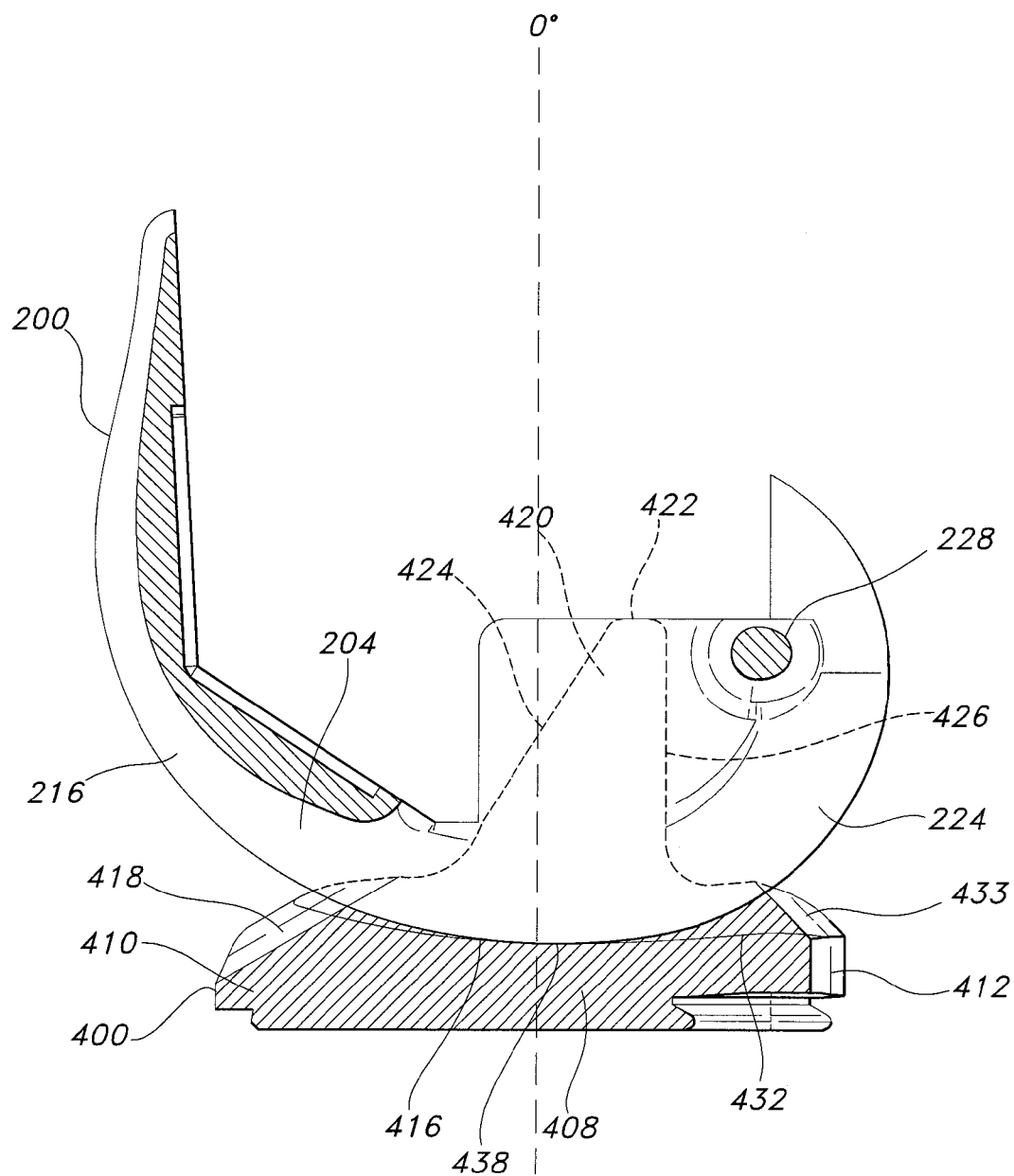
FIG. 7 is a side cross-sectional view of a partially assembled knee prosthesis according to an embodiment of the invention showing full extension of the knee.
Figure 8:
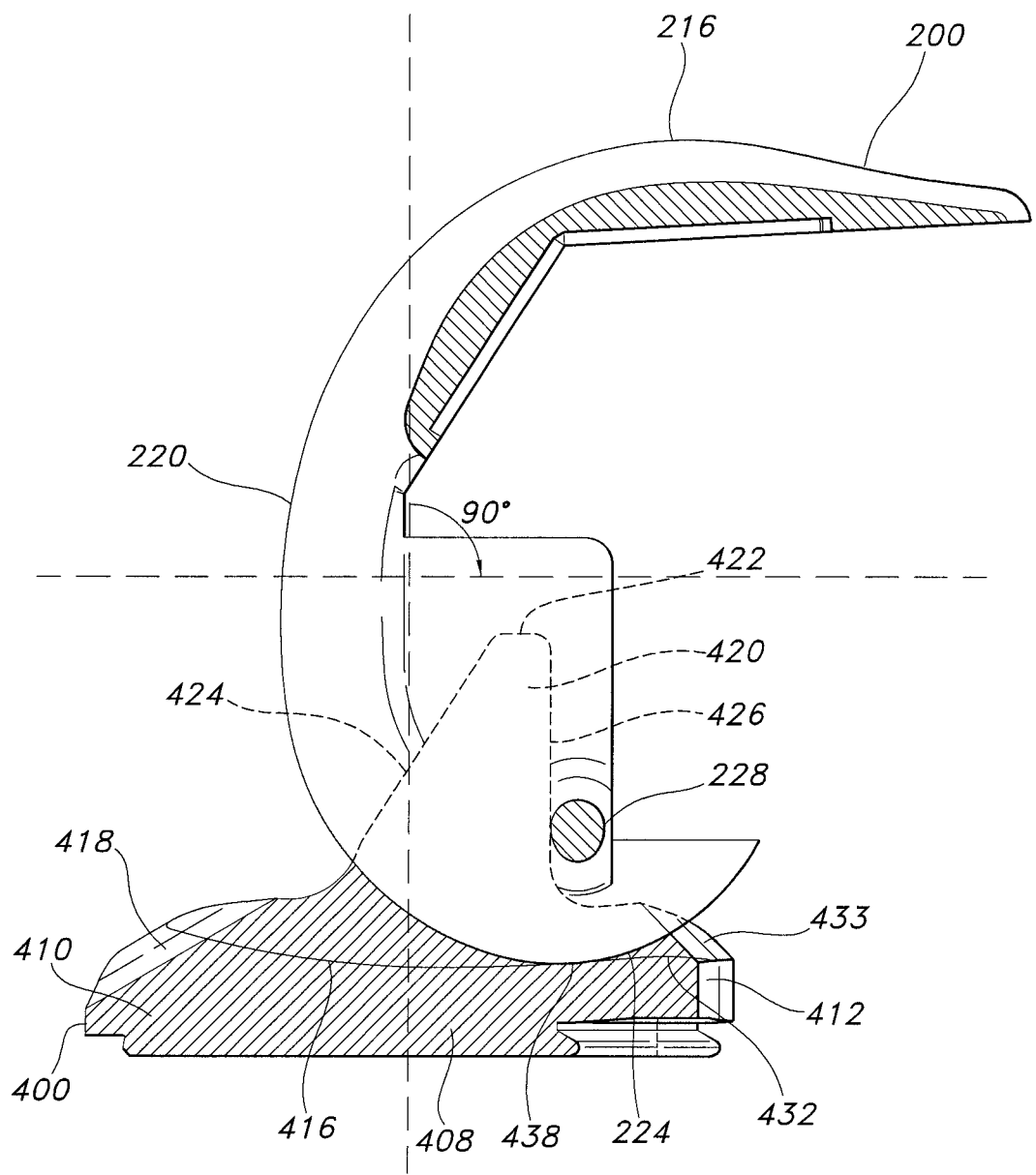
FIG. 8 is a side cross-sectional view of a partially assembled knee prosthesis according to an embodiment of the invention showing flexion of the knee to 90°.

For example, the particular knee prosthesis 100 of FIG. 7 is shown as it would appear when the knee is fully extended. Other various maximal angles of extension are possible with various prostheses. The distal portions 218, 220 of the medial and lateral condylar portions 202, 204 are in contact with the medial and lateral concavities 414, 416. When the knee is flexed to approximately 90°, as shown in FIG. 8, the posterior portions 222, 224 of the medial and lateral condylar portions 202, 204 are in contact with the medial and lateral concavities 414, 416. The cam 228 is also in contact with the posterior surface 426 of the central post 420 of femoral component 400.

Figure 9:
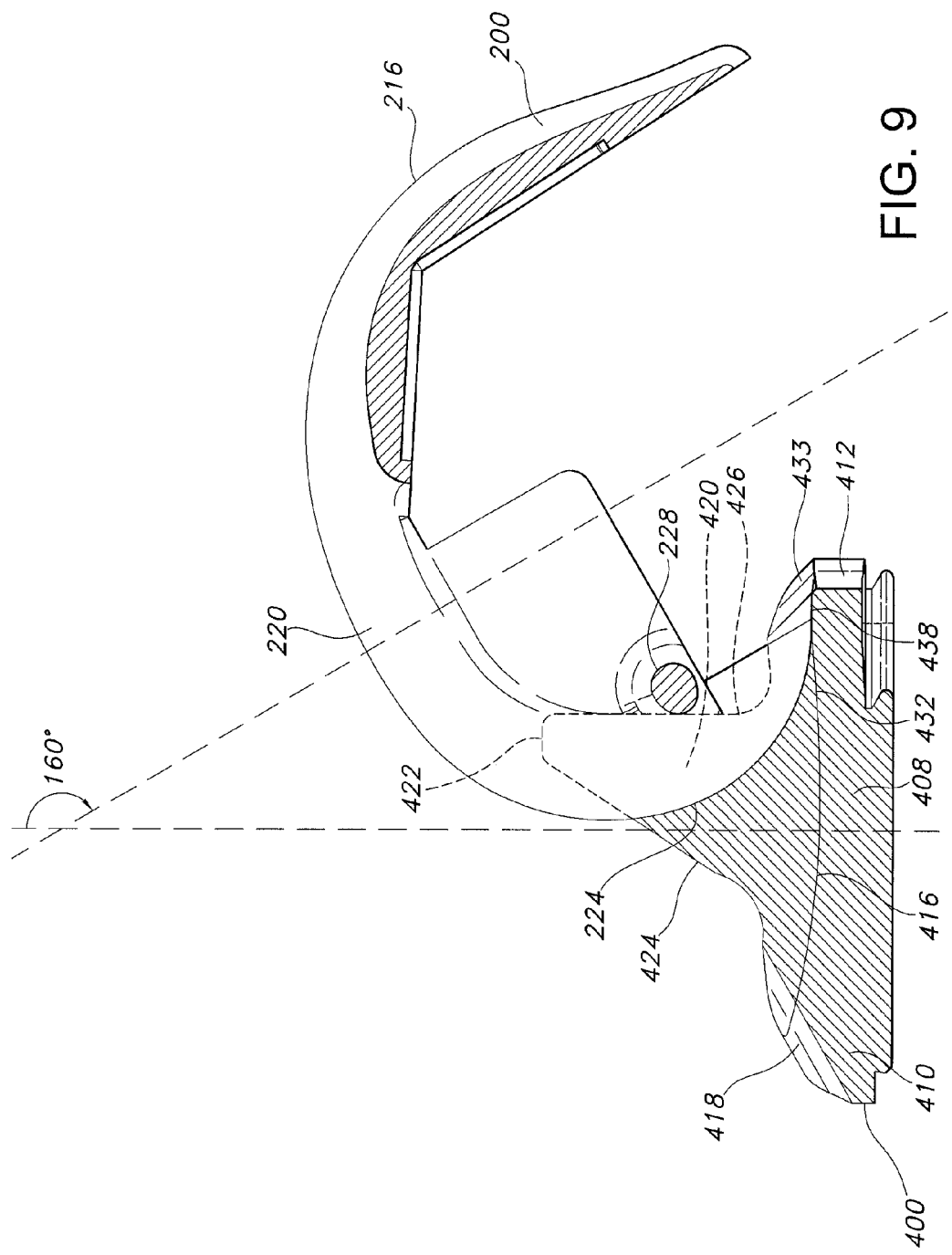
FIG. 9 is a side cross-sectional view of a partially assembled knee prosthesis according to an embodiment of the invention showing flexion of the knee to 160°.

At approximately 120° to 140° flexion, the femoral component 200 begins to contact the articular blend 432 on the posterior side 412 of the insert 400. However, as shown in FIG. 9, the knee can be flexed to approximately 160° before the femoral component 200 fully contacts the intersection edge of the articular blend 432 and the curved posterior surface 433 and additional flexion is difficult or impossible. The increased flexion is achieved primarily by the articular blend 432 which results in a transition on the proximal surface 402 of the insert 400 of the sagittal concave curvature of the lateral and medial concavities 414, 416 into a convex surface that maintains the coronal curvature of the medial and lateral condylar portions 202, 204. The articular blend 432 moves the 160° femorotibial contact point 438 anteriorly on the insert 400 and distally on the femoral component 200. Thus, edge loading is reduced and material that may impinge on the femoral posterior cortex (not shown) in deep flexion has been removed. The anterior shift in the femorotibial contact point 438 increases the dislocation safety factor in deep flexion, making dislocation less likely. However, if the posterior portion 224 of the lateral condylar portion 204 should rotate off the insert 400, as may occur in the normal knee in deep flexion, it will more easily engage the lateral concavity 416 as the knee returns to extension.

The foregoing description is provided for describing various embodiments and structures relating to the invention. Various modifications, additions and deletions may be made to these embodiments and/or structures without departing from the scope and spirit of the invention.

What is claimed:

1. An articular insert for use with a knee prosthesis, comprising:
    (a) a medial contact portion configured to articulate against a medial femoral condyle, comprising a posterior edge and a curvature in a sagittal plane which transitions, in a posterior direction, from a concave surface into a convex surface; and
    (b) a lateral contact portion configured to articulate against a lateral femoral condyle, comprising a posterior edge and a curvature in a sagittal plane which transitions, in a posterior direction, from a concave surface into a convex surface;
    wherein the convex surface of each contact portion is positioned at the posterior edge of each contact portion, and the convex surface of each contact portion extends along the contact portion to increase the amount of flexion allowed by the knee prosthesis.

2. The articular insert of claim 1, wherein the articular insert is part of a tibial implant.

3. The articular insert of claim 1, wherein the articular insert is part of an insert configured to fit between a femoral component and a tibial implant.

4. The articular insert of claim 1, wherein the curvature in a sagittal plane of the medial contact portion and the curvature in a sagittal plane of the lateral contact portion are at a contact interface of a femoral component and the articular insert when the knee is flexed approximately 120 degrees to 140 degrees.

5. The articular insert of claim 1, further comprising a post configured to provide support to a posterior side of a femoral component.

6. The articular insert of claim 5, wherein the post comprises a tapered anterior surface.

7. The articular insert of claim 1, wherein the articular insert further comprises a curved anterior surface configured to minimize impingement of an intercondylar notch of a femoral component when the knee prosthesis is hyperextended.

8. The articular insert of claim 1, wherein the articular insert further comprises a curved posterior surface configured to minimize impingement of a posterior cortex of a femur when the knee is flexed approximately 130 degrees or greater.

9. The articular insert of claim 1, wherein the curvature in a sagittal plane of both the medial and lateral contact portions comprises a sagittal radius of about 1.0 inch.

10. The articular insert of claim 1, wherein the convex surface of the lateral contact portion is configured to engage an externally rotated lateral posterior condyle of a femoral component in deep flexion as the knee returns to extension.

11. The articular insert of claim 1, wherein the convex surface of the curvature in a sagittal plane of both the medial and lateral contact portions comprises an area where material is removed from the posterior edge of the structure.

12. The articular insert of claim 1, wherein the convex surface of the curvature in a sagittal plane of both the medial and lateral contact portions is configured to lower the posterior edge of the structure and help maintain joint space.

13. The articular insert of claim 1, wherein the concave surface of each of the lateral contact portion and the medial contact portion is defined by at least a first curvature in a coronal plane having a radius of curvature of approximately 1.05 inches.

14. The articular insert of claim 13, wherein the concave surface of each of the lateral contact portion and the medial contact portion is defined by at least a second curvature in a sagittal plane having a radius of curvature of approximately 2.88 to 3.05 inches.

15. The articular insert of claim 14, wherein the first curvature and the second curvature that define the concave surface of the lateral contact portion intersect at approximately the center of the concave surface of the lateral contact portion, and the first curvature and the second curvature that define the concave surface of the medial contact portion intersect at approximately the center of the concave surface of the medial contact portion.

16. The articular insert of claim 14, wherein the concave surface of each of the lateral contact portion and the medial contact portion is defined by at least an additional curvature in a sagittal plane having a radius of curvature of approximately 2.88 to 3.05 inches.

17. The articular insert of claim 1, wherein the medial and lateral contact portion curvatures are identical.

18. An articular insert for use with a knee prosthesis, comprising:
(a) a medial contact portion configured to articulate against a medial femoral condyle, comprising a curvature in a sagittal plane which transitions, in a posterior direction, from a concave surface into a convex surface; and
(b) a lateral contact portion configured to articulate against a lateral femoral condyle, comprising a curvature in a sagittal plane which transitions, in a posterior direction, from a concave surface into a convex surface;

wherein the curvature in a sagittal plane of the medial contact portion is substantially the same shape as the curvature in a sagittal plane of the lateral contact portion, and the convex surface of each contact portion extends along the contact portion to increase the amount of flexion allowed by the knee prosthesis.

19. The articular insert of claim 18, wherein the articular insert is part of a tibial implant.

20. The articular insert of claim 18, wherein the articular insert is part of an insert configured to fit between a femoral component and a tibial implant.

21. The articular insert of claim 18, wherein the curvature in a sagittal plane of the medial contact portion and the curvature in a sagittal plane of the lateral contact portion are at a contact interface of a femoral component and the articular insert when the knee is flexed approximately 120 degrees to 140 degrees.

22. The articular insert of claim 18, further comprising a post configured to provide support to a posterior side of a femoral component.

23. The articular insert of claim 22, wherein the post comprises a tapered anterior surface.

24. The articular insert of claim 18, wherein the articular insert further comprises a curved anterior surface configured to minimize impingement of an intercondylar notch of a femoral component when the knee prosthesis is hyperextended.

25. The articular insert of claim 18, wherein the articular insert further comprises a curved posterior surface configured to minimize impingement of a posterior cortex of a femur when the knee is flexed approximately 130 degrees or greater.

26. The articular insert of claim 18, wherein the curvature in a sagittal plane of both the medial and lateral contact portions comprises a sagittal radius of about 1.0 inch.

27. The articular insert of claim 18, wherein the convex surface of the lateral contact portion is configured to engage an externally rotated lateral posterior condyle of a femoral component in deep flexion as the knee returns to extension.

28. The articular insert of claim 18, wherein the convex surface of the curvature in a sagittal plane of both the medial and lateral contact portions comprises an area where material is removed from the posterior edge of the structure.

29. The articular insert of claim 18, wherein the convex surface of the curvature in a sagittal plane of both the medial and lateral contact portions is configured to lower the posterior edge of the structure and help maintain joint space.

30. The articular insert of claim 18, wherein the concave surface of each of the lateral contact portion and the medial contact portion is defined by at least a first curvature in a coronal plane having a radius of curvature of approximately 1.05 inches.

31. The articular insert of claim 30, wherein the concave surface of each of the lateral contact portion and the medial contact portion is defined by at least a second curvature in a sagittal plane having a radius of curvature of approximately 2.88 to 3.05 inches.

32. The articular insert of claim 31, wherein the first curvature and the second curvature that define the concave surface of the lateral contact portion intersect at approximately the center of the concave surface of the lateral contact portion, and the first curvature and the second curvature that define the concave surface of the medial contact portion intersect at approximately the center of the concave surface of the medial contact portion.

33. The articular insert of claim 30, wherein the concave surface of each of the lateral contact portion and the medial contact portion is defined by at least an additional curvature in a sagittal plane having a radius of curvature of approximately 2.88 to 3.05 inches.

34. The articular insert of claim 18, wherein the medial and lateral contact portions curvatures are identical.

35. An articular insert for use in connection with a knee prosthesis, the knee prosthesis comprising a femoral component and a tibial component, the articular insert comprising:

an articular insert comprising a medial contact portion configured to provide an articular surface for a medial condyle of the femoral component, a lateral contact portion configured to provide an articular surface for a lateral condyle of the femoral component, the medial and lateral contact portions having substantially the same shape, each of the medial and lateral contact portions comprising a curvature in a sagittal plane which transitions, in a posterior direction, from a concave surface into a convex surface at a contact point between the femoral component and the articular insert when the femoral component is flexed at 120 degrees to 140 degrees, the convex surface of each contact portion extending along the contact portion to increase the amount of flexion allowed by the knee prosthesis.

36. The articular insert of claim 35, wherein the articular insert is part of a tibial implant.

37. The articular insert of claim 35, wherein the articular insert is part of an insert configured to fit between a femoral component and a tibial implant.

38. The articular insert of claim 35, wherein the curvature in a sagittal plane of the medial contact portion and the curvature in a sagittal plane of the lateral contact portion are at a contact interface of a femoral component and the articular insert when the knee is flexed approximately 120 degrees to 140 degrees.

39. The articular insert of claim 35, further comprising a post configured to provide support to a posterior side of a femoral component.

40. The articular insert of claim 39, wherein the post comprises a tapered anterior surface.

41. The articular insert of claim 35, wherein the articular insert further comprises a curved anterior surface configured to minimize impingement of an intercondylar notch of a femoral component when the knee prosthesis is hyperextended.

42. The articular insert of claim 35, wherein the articular insert further comprises a curved posterior surface configured to minimize impingement of a posterior cortex of a femur when the knee is flexed approximately 130 degrees or greater.

43. The articular insert of claim 35, wherein the curvature in a sagittal plane of both the medial and lateral contact portions comprises a sagittal radius of about 1.0 inch.

44. The articular insert of claim 35, wherein the convex surface of the lateral contact portion is configured to engage an externally rotated lateral posterior condyle of a femoral component in deep flexion as the knee returns to extension.

45. The articular insert of claim 35, wherein the convex surface of the curvature in a sagittal plane of both the medial and lateral contact portions comprises an area where material is removed from the posterior edge of the structure.

46. The articular insert of claim 35, wherein the convex surface of the curvature in a sagittal plane of both the medial and lateral contact portions is configured to lower the posterior edge of the structure and help maintain joint space.

47. The articular insert of claim 35, wherein the concave surface of each of the lateral contact portion and the medial contact portion is defined by at least a first curvature in a coronal plane having a radius of curvature of approximately 1.05 inches.

48. The articular insert of claim 47, wherein the concave surface of each of the lateral contact portion and the medial contact portion is defined by at least a second curvature in a sagittal plane having a radius of curvature of approximately 2.88 to 3.05 inches.

49. The articular insert of claim 48, wherein the first curvature and the second curvature that define the concave surface of the lateral contact portion intersect at approximately the center of the concave surface of the lateral contact portion, and the first curvature and the second curvature that define the concave surface of the medial contact portion intersect at approximately the center of the concave surface of the medial contact portion.

50. The articular insert of claim 47, wherein the concave surface of each of the lateral contact portion and the medial contact portion is defined by at least an additional curvature in a sagittal plane having a radius of curvature of approximately 2.88 to 3.05 inches.

51. The articular insert of claim 35, wherein the medial and lateral contact portion curvatures are identical.

52. A high flexion articular insert, comprising:

a lateral contact portion configured to contact a lateral condylar structure and a medial contact portion configured to contact a medial condylar structure, each of the lateral and the medial contact portions comprising a curvature in a sagittal plane which transitions, in a posterior direction, from a concave surface into a convex surface, wherein the curvatures in a sagittal plane have substantially the same shape, and wherein the convex surface of each contact portion is positioned at a posterior edge of the contact portion, and the convex surface of each contact portion extends along the contact portion to increase the amount of flexion allowed by the medial and lateral condylar structures; and a post configured to provide posterior support to a femoral component, the post configured to minimize impingement on a patellar component when the knee is flexed approximately 130 degrees or greater.

53. The high flexion articular insert of claim 52, wherein the medial and lateral contact portions curvatures are identical.

* * * * *